(12) United States Patent
Carr

(10) Patent No.: US 6,496,738 B2
(45) Date of Patent: *Dec. 17, 2002

(54) DUAL FREQUENCY MICROWAVE HEATING APPARATUS

(76) Inventor: Kenneth L. Carr, 30 Woodside Rd., Harvard, MA (US) 01451

( * ) Notice: Subject to any disclaimer, the term of this patent is extended or adjusted under 35 U.S.C. 154(b) by 67 days.

This patent is subject to a terminal disclaimer.

(21) Appl. No.: 09/777,971

(22) Filed: Feb. 6, 2001

(65) Prior Publication Data

US 2001/0016762 A1 Aug. 23, 2001

Related U.S. Application Data

(63) Continuation-in-part of application No. 09/368,179, filed on Aug. 4, 1999, now Pat. No. 6,210,367, which is a continuation-in-part of application No. 08/977,747, filed on Nov. 25, 1997, now Pat. No. 6,146,359, which is a continuation-in-part of application No. 08/524,392, filed on Sep. 6, 1995, now Pat. No. 5,690,614.

(51) Int. Cl.$^7$ .................................................. A61F 7/00
(52) U.S. Cl. ....................... 607/101; 607/102; 604/114
(58) Field of Search ............................. 607/96, 98–102, 607/105; 604/113, 114

(56) References Cited

U.S. PATENT DOCUMENTS

| | | | |
|---|---|---|---|
| 4,557,272 A | * 12/1985 | Carr | 600/549 |
| 4,798,215 A | 1/1989 | Turner | |
| 4,860,752 A | 8/1989 | Turner | |
| 5,176,146 A | * 1/1993 | Chive et al. | 374/122 |
| 5,188,602 A | 2/1993 | Nichols | |
| 5,344,435 A | 9/1994 | Turner et al. | |
| 5,688,050 A | * 11/1997 | Sterzer et al. | 374/121 |
| 5,693,082 A | 12/1997 | Warner et al. | |
| 6,210,367 B1 | 4/2001 | Carr | |

FOREIGN PATENT DOCUMENTS

EP    0 401 995 A2    12/1990

* cited by examiner

Primary Examiner—Roy D. Gibson
(74) Attorney, Agent, or Firm—Cesari and McKenna LLP

(57) ABSTRACT

Microwave heating apparatus for heating fluid or tissue includes an elongated catheter for placement adjacent to high/dielectric high loss organic fluid or tissue in a patient. The catheter has a distal end and a proximal end and includes an antenna adjacent to the distal end and a cable having one end connected to the antenna and a second end. A transmitter provides a transmitter signal capable of heating the fluid or tissue and a first receiver receives a first signal indicative of thermal radiation from a first depth in the fluid or tissue, producing a first output signal in response thereto. There is also a second receiver for receiving a second signal indicative of thermal radiation from a second depth in the fluid or tissue, producing a second output signal in and response thereto. The apparatus also includes active and passive diplexers connected in series between the transmitter and the second end of the cable. A controller controls the active diplexer so that when the transmitter is transmitting, the first signal is coupled to the passive diplexer but not to the second receiver and when the transmitter is not transmitting, a second signal from the passive diplexer is coupled to the second receiver but not to the transmitter. During operation of the apparatus, the passive diplexer couples the transmitter signal only to the antenna while coupling a first signal from the antenna only to the first receiver so that the apparatus can heat the fluid or tissue and determine the actual temperatures of the fluid or tissue at two different depths.

15 Claims, 3 Drawing Sheets

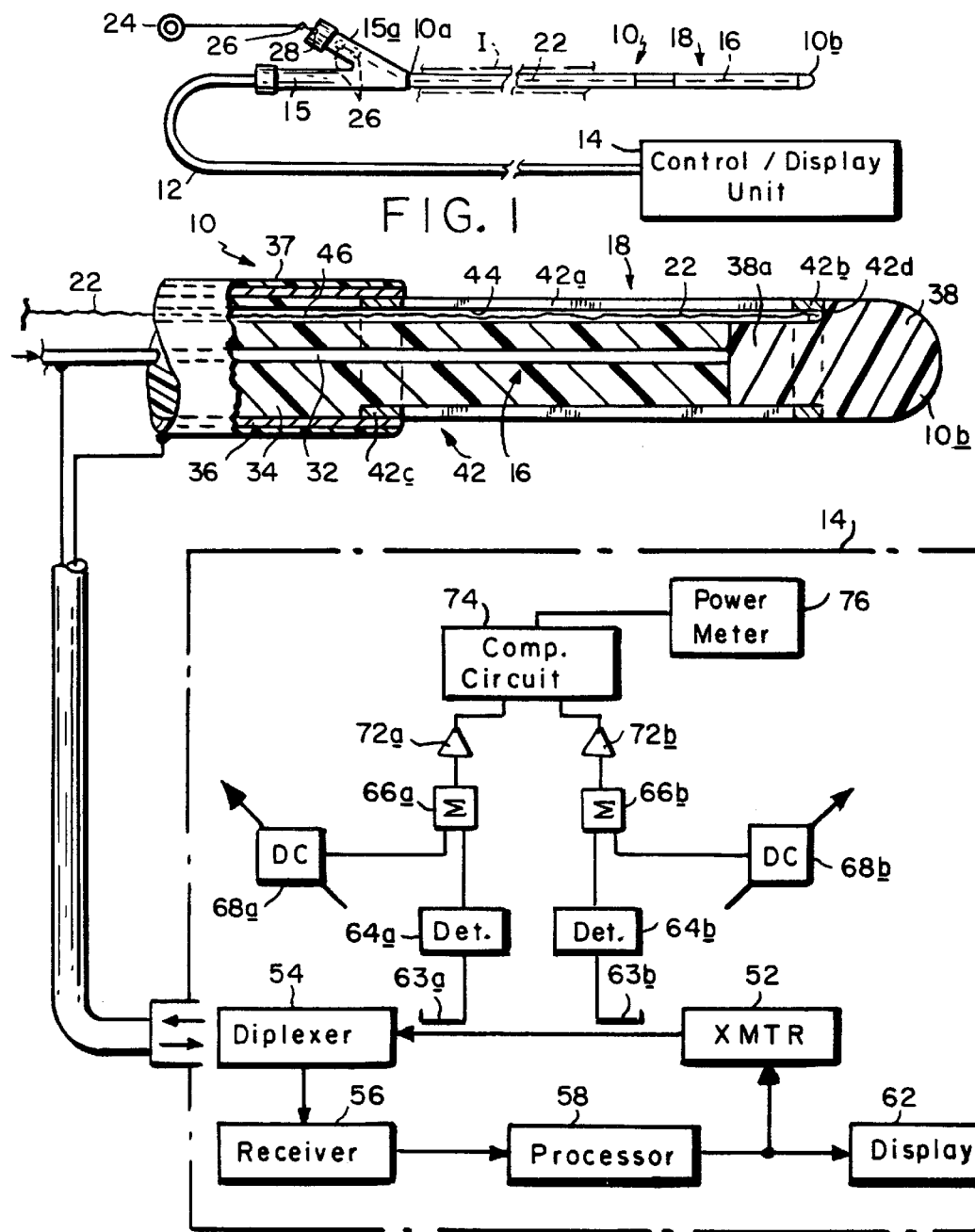

DUAL FREQUENCY MICROWAVE HEATING APPARATUS

RELATED APPLICATIONS

This application is a continuation-in-part of Ser. No. 09/368,179, filed Aug. 4, 1999, now U.S. Pat. No. 6,210,367, which is a continuation-in-part of Ser. No. 08/977,747, filed Nov. 25, 1997, now U.S. Pat. No. 6,146,359, which is a continuation-in-part of Ser. No. 08/524,392, filed Sep. 6, 1995, now U.S. Pat. No. 5,690,614.

BACKGROUND OF THE INVENTION

This invention relates to microwave heating apparatus. It relates more particularly to microwave apparatus including a catheter capable of being introduced into a patient's blood vessel or body cavity to provide uniform and controlled heating of fluid or tissue within the patient. The invention has particular application as an intravascular blood warmer for raising the body core temperature of a hypothermic trauma patient and so the invention will be described primarily in that context. It should be understood, however, that aspects of the invention have equal application in other contexts such as benign prostatic hyperplasia (BPH) ablation and myocardial ablation.

Hypothermia in trauma patients (i.e., body core temperature less than 35° C.), has been shown to be associated with high mortality. According to studies, trauma patients having a temperature less than 34° C. have a 60% mortality and those patients with a temperature less than 32° C. have a 100% mortality. The effects of hypothermia on trauma patients are numerous. For example, a decrease in core temperature results in decreased mental status, decrease heart rate and cardiac output and diminished renal blood flow.

Hypothermia also results in prolonged clotting times and portal sequestration of platelets causing peripheral thrombocytopenia as well as decreased platelet finction. The resultant coagulopathy may make futile all attempts at surgical control of traumatic bleeding.

There are currently several methods of rewarming a trauma patient in general use today. These include use of warm resuscitation fluids, airway rewarming, heating blankets, overhead radiant warmers, body cavity lavage, continuous arteriovenous rewarming (CAVR) and cardiopulmonary bypass. The most effective method of rewarming is currently cardiopulmonary bypass, but this technique is often unavailable and is technically difficult to perform. CAVR has been shown to be,much more efficient than other standard rewarming techniques, but it requires cannulation of both the femoral artery and vein in order to connect the patient to a conventional external heat exchanger and it is somewhat work intensive. Furthermore, it results in loss of blood because a considerable amount of fluid is required in order to fill up or prime the various IV tubes connected to the warmer.

It would be desirable, therefore, to be able to provide a simple, efficient means of rewarming trauma patients, especially soldiers in combat who are significantly injured and therefore at risk for developing hypothermia controlled intracorporeal heating for other reasons is also a desirable objective.

SUMMARY OF THE INVENTION

Accordingly, it is an object of the present invention to provide an improved technique for controlledly heating fluid or tissue in a patient.

Another object of the invention is to provide microwave warming apparatus for efficiently heating or rewarming fluid or tissue in a patient.

A further object of the invention is to provide such apparatus which provides uniform and controlled heating in a hypothermic trauma patient.

Another object is to provide such warming apparatus which requires only a single venous connection to a patient and which minimizes patient blood loss.

An additional object of the invention is to provide an improved intravascular microwave warming catheter which minimizes blockage of, and injury to, the blood vessel in which it is placed.

A further object of the invention is to provide intravascular microwave warming apparatus which simultaneously monitors accurately the temperature of the blood during the warming process.

Another object of the invention is to provide microwave apparatus to controlledly ablate or necrose tissue within a patient.

Other objects will, in part, be obvious and will, in part, appear hereinafter.

The invention accordingly comprises the several steps and the relation of one or more of such steps with respect to each of the others, and the apparatus embodying the features of construction, combination of elements and arrangement of parts which are adapted to effect such steps, all is exemplified in the following detailed description, and the scope of the invention would be indicated in the claims.

Briefly, the intravascular blood warming technique specifically disclosed herein is intended to provide uniform and controlled heating in a hypothermic patient using microwave apparatus which safely and efficiently warms the patient's blood in order to raise the patient's body core temperature.

The warming apparatus comprises a relatively long, somewhat flexible intravascular catheter capable of being threaded through a conventional introducer to a major blood vessel such as the superior or inferior vena cava. At its distal end, the catheter incorporates an antenna and an expandable stand-off device which prevents the distal end of the catheter, and more particularly the antenna, from contacting the wall of the blood vessel and potentially overheating tissue at that wall. A single cable extending from the proximal end of the catheter is connected to an extracorporeal control and display unit which supplies power to and receives temperature-indicating signals from the catheter.

The control and display unit includes a microwave transmitter which produces a signal having a suitable heating frequency. That signal is applied by way of a diplexer to the cable leading to the antenna in the catheter. This causes the antenna to emit electromagnetic radiation capable of heating high dielectric/high loss organic material such as blood in the vicinity of the catheter.

Also, connected to the diplexer in the control and display unit is a microwave receiver preferably in the form of a radiometer. As is well known, radiometry is a technique for measuring electromagnetic radiation considered as thermal radiation. The single antenna in the catheter is able to detect the microwave radiation emitted by the material surrounding the catheter and that microwave signal is applied by way of the cable and diplexer to the receiver which produces an electrical signal indicative of the temperature of that material. That signal is applied by way of a processor to a display in the control and display unit which thereupon provides a visible indication of that temperature. That temperature-indicating signal can also be used to enable the processor to control the transmitter so as to effect controlled heating of the material surrounding the catheter. As we shall see also, the control and display unit includes means for detecting whether the aforementioned stand-off device in the catheter is open or closed to ensure that the catheter is in the correct position in the blood vessel before the catheter's antenna is activated.

As will be described in more detail later, the diplexer in the control and display unit allows for the separation of the relatively low heating frequency of the transmitter from the much higher radiometer frequency. Resultantly, the apparatus can use a common antenna and cable connection to the control and display unit to both transmit (heat) and receive (measure temperature). Thus, the diplexer and associated radiometer eliminate the need for thermocouples or thermistors in the catheter thereby minimizing the cost of, and improving the performance and safety record of, the catheter. It should be emphasized in this connection that this cost and performance comparison is not being made between just a radiometer and a thermocouple, but rather with all of the ancillary parts such as wires, connectors and amplifiers that have to support the thermocouple. Elimination of all of these parts enhances the flexibility of the catheter and greatly improves the overall reliability and maintenance record of the apparatus.

Most importantly, since the present apparatus senses temperature using radiometry, the temperature sensed is the actual temperature of the blood surrounding the catheter rather than the catheter tip temperature as would be the case if the catheter incorporated a thermocouple or thermister for temperature detection and control.

Similar devices incorporating the invention can be used in other applications. In tissue ablation, for example, the configuration of the catheter depends upon the body cavity being accessed. Thus, to treat BPH, a transurethral catheter or probe is used which may incorporate a conventional helical antenna and receive sufficient power to raise the patient's intraprostatic temperature sufficiently and for a sufficient time to selectively necrose the BPH. Such a catheter typically incorporates a cooling circuit adjacent the antenna to ensure that the patient's urethra is not heated above a safe temperature, and an expandable balloon to properly position the catheter; see my application Ser. No. 09/476,201, filed Jan. 3, 2000, the contents of which is hereby incorporated herein by reference.

Transurethral microwave heating apparatus incorporating this invention would allow a common antenna in the catheter or probe to provide both heating and measurement of temperature, thereby eliminating the requirement of thermocouples and wires and allowing closer control over actual tissue temperature, as well as providing a positive indication of the condition of the catheter's expandable device. In this case, the expandable device, when open, would seat against the neck of the patient's bladder to properly locate the catheter or probe.

When used for myocardial ablation, the present apparatus would include a catheter with an antenna and an expandable stand-off device and capable of being threaded into a patient's heart muscle in order to controlledly heat heart tissue in order to necrose said tissue. In this application, the expandable device is used to center the catheter.

Other applications for the invention may be envisioned.

BRIEF DESCRIPTION OF THE DRAWINGS

For a fuller understanding of the nature and objects of the invention, reference should be made to the following detailed description taken in connection with the accompanying drawings, in which:

FIG. 1 is a diagrammatic view of intracorporeal microwave warming apparatus incorporating the invention;

FIG. 2 is a fragmentary sectional view on a larger scale, with some parts shown diagrammatically, of the FIG. 1 apparatus showing the apparatus' stand-off device in its closed position;

DETAILED DESCRIPTION OF ILLUSTRATIVE EMBODIMENTS

Figure 3:
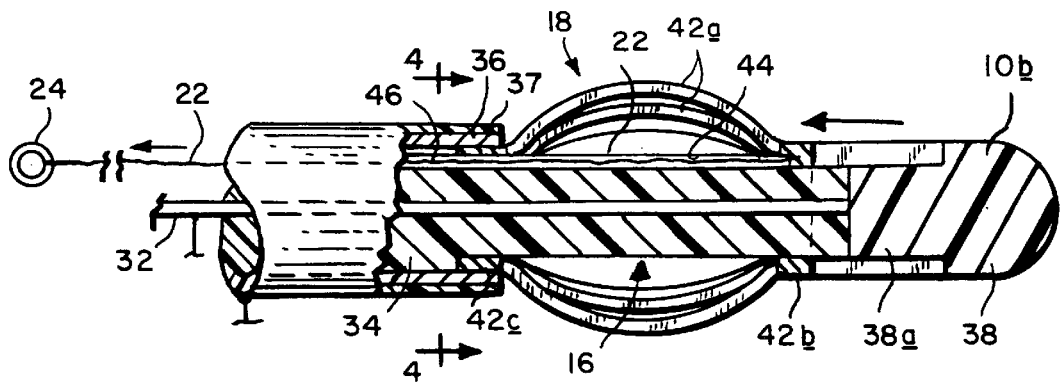
FIG. 3 is a similar view with the apparatus' stand-off device shown in its open or expanded position.

Referring to FIG. 1 of the drawings, warming apparatus suitable for treating hypothermia comprises a relatively long catheter 10 connected by a single coaxial cable 12 to a control and display unit 14. Catheter 10, which may be designed as a low-cost disposable device, has a proximal end 10a to which cable 12 is connected by way of a tubular fitting 15 and a distal end or tip 10b. Catheter 10 has a small diameter and is relatively flexible so that it can be threaded along a conventional introducer, e.g., 8.5 French, 1 indicated in phantom at 1 in FIG. 1, allowing the distal end 10b of the catheter to be placed at a selected position in a patient's blood vessel V (FIG. 4), such as the superior or inferior vena cava. Typically, vessel V is accessed via a vein in the patient's neck.

Figure 4:
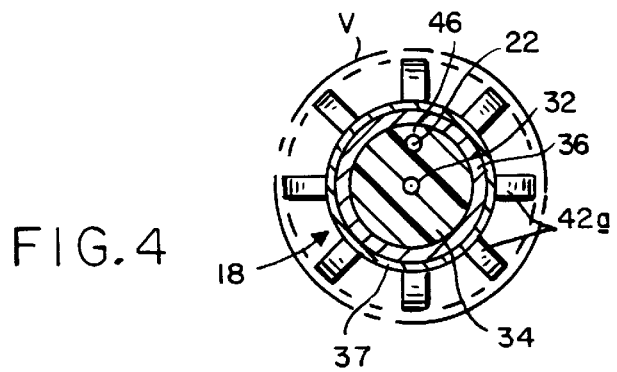
FIG. 4 is a sectional view taken along line 4—4 of FIG. 3.

When the catheter 10 is properly positioned as aforesaid, the control and display unit 14 supplies power to a microwave antenna 16 located adjacent to the distal end 10b of the catheter causing the antenna to emit electromagnetic radiation which warms the blood in the blood vessel surrounding the antenna. Preferably, catheter 10 also includes a stand-off device indicated at 18 adjacent to the antenna which can be moved from a closed position illustrated in FIGS. 1 and 2 and an open or expanded position shown in FIGS. 3 and 4. When the stand-off device 18 is closed, it is more or less cylindrical and has substantially the same cross-sectional size as the remainder of the catheter so that it does not interfere with the movement of the catheter along introducer 1 to and from the patient's blood vessel V. On the other hand, when the device 18 is moved to its open or expanded position upon placement of the catheter at the proper location in the patient's blood vessel V as shown in FIG. 4, the device 18 spaces the antenna 16 from the wall of that vessel thereby preventing excessive heating of and damage to, the tissue comprising that wall.

In accordance with the invention, means are provided for moving the stand-off device 18 between its open and closed positions. In the catheter depicted in FIG. 1, the stand-off device 18 has an inherent bias or resilience which normally maintains that device in its closed position shown in FIG. 2. The device may be moved from that position to its open position shown in FIGS. 3 and 4 by means of a flexible cord 22 which extends from device 18 along the catheter and through a tubular branch 15a of fitting 15 to a ring 24. By pulling on the cord 22 using ring 24, the device 18 may be moved to its open position. The device can be maintained in that position by engaging one of a series of beads 26 on cord 22 in a notch 28 in the free end of the fitting branch 15a as shown in FIG. 1. When the tension on cord 22 is relieved, the stand-off device 18 will resume its normal cylindrical shape best seen in FIG. 2.

As shown in FIG. 2, the catheter 10 comprises a central conductor 32 surrounded by a cylindrical body 34 of a suitable low loss dielectric material. Surrounding the dielectric body 34 is an outer conductor 36. At fitting 15, the proximal ends of conductors 32 and 36 are connected to the inner and outer conductors of coaxial cable 12. Preferably, a protective coating 37, e.g. of PTFE, covers outer conductor 36.

As shown in FIG. 2, At distal end segment of the catheter 10, the inner conductor 32 and dielectric body 34 extend beyond the outer conductor 36 to form the microwave antenna 16 which, in this case, is a monopole producing a relatively long radiation pattern. In some applications, a helical antenna may be used; see U.S. Pat. No. 4,583,556. Furthermore, the projecting segment of the body 34 has a reduced cross-section to accommodate and provide clearance for the stand-off device 18. The distal end 10b of the catheter is actually formed by a rounded low loss dielectric button 38 having a cylindrical stem 38a which has the same diameter as the distal end of the dielectric body 34 so that the stem 38a can be butted and secured to the distal end of body 34 as shown in FIG. 2.

The stand-off device 18 comprises a cylindrical sleeve 42 of low dielectric/low loss material having an inside diameter which is slightly larger than the reduced diameter of body 34 and the button stem 38a. Sleeve 42 is slitted along its length to provide a circular array of flexible, resilient ribs 42a which extend between a distal annular sleeve end segment 42b encircling button stem 38a and a proximal annular sleeve end segment 42c encircling dielectric body 34 under the distal end of outer conductor 36. That is, the reduction in cross section of the dielectric body 34 extends under the distal end of outer conductor 36 to accommodate the sleeve segment 42c. End segment 42c is fixed by an adhesive or other means, while end segment 42b is slidable.

As best seen in FIG. 2, the dielectric body 34 and button stem 38a are grooved lengthwise at 44, that groove connecting with a longitudinal passage 46 in body 34 which extends to the fitting branch 15a to accommodate the cord 22. The distal end of cord 22 attached to a radially inner nub 42d on the slidable end segment 42b of sleeve 42, which nub slides along groove 44. Normally, sleeve 42 reposes in its closed position illustrated in FIG. 2, i.e., it has a cylindrical shape which falls within the envelope of the catheter 10. Therefore, the catheter is able to pass through introducer I (FIG. 1). However, when tension is applied to cord 22, the distal end segment 42b of the sleeve slides toward the proximal end segment 42c thereof causing the sleeve ribs 42a to flex and bow outward as shown in FIGS. 3 and 4, thereby greatly increasing the cross-section of the stand-off device 18. In fact, the ribs 42a may be flexed to an extent that they contact the wall of the blood vessel V in which the catheter 10 is placed as shown in FIG. 4 so that the catheter antenna 16 is maintained in spaced relation to the vessel wall.

It is important to note that when the stand-off device 18 is in its open position shown in FIGS. 3 and 4, it does not appreciably obstruct blood flow through the patient's blood vessel V. Therefore, no hot spots are created in the blood adjacent antenna 16 as could occur if catheter 10 incorporated a conventional balloon-type stand-off device. In other words, blood is free to flow through and around the expanded ribs 42a so that there is no development of slow moving or stagnant "pools" of blood around the catheter that could be heated excessively by antenna 16.

When the tension on cord 22 is relieved, the resilient sleeve ribs 42a tend to resume their unflexed linear state so that the sleeve resumes it natural cylindrical shape thereby enabling the stand-off device 18 and catheter 10 as a whole to again pass through the introducer 1 (FIG. 1).

Still referring to FIG. 2, the control and display unit 14 is similar to the one disclosed in the above-identified patent applications, the contents of which are hereby incorporated by reference herein. More particularly, unit 14 comprises a microwave transmitter 52 which is preferably a solid state programmable transmitter which may operate at 915 MHz ($\lambda T$) and have a maximum power output of 0 to 120 watts. Such a transmitter is available from Microwave Medical Systems, Inc., Acton, MA (Part No. 190972). That transmitter provides, if desired, short-term operation with battery back up and automatic battery recharging when the unit is plugged into an operative AC outlet.

The output from the transmitter is coupled to coaxial cable 12 by way of a diplexer 54. That transmitted power causes antenna 16 to emit electromagnetic radiation. As the blood surrounding catheter 10 absorbs energy, its temperature is elevated.

The same antenna also detects the thermal radiation emitted by that fluid and applies a corresponding electrical signal via diplexer 54 to a microwave receiver 56, to wit: a radiometer, in control and display unit 14. A suitable radiometer is available from Microwave Medical Systems, Inc., Acton, MA (Part No. RAD-G1) It has a physical volume of only about 2 cubic inches and weighs only 3 ounces. It has a radiometer frequency of 3.7 to 4.2 GHz, with a center frequency of 4.0 GHz ($\lambda R$).

Due to the presence of the diplexer 54, the receiver 56 detects only that energy associated with the blood being heated. The temperature-indicating signal from receiver 56 may then be processed by a processor 58 in unit 14 to maintain the blood in vessel V at a selected temperature, e.g., normal body temperature, or to warm the blood according to a selected temperature vs time profile programmed into processor 58.

The processor 58 also controls a display 62 in unit 10 which can display in real time the patient's body core temperature and other useful information such as the selected temperature vs time profile, diagnostic data and the like.

Figure 5:
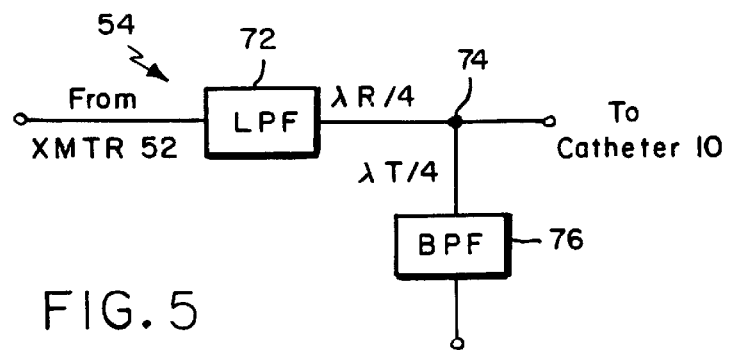
FIG. 5 is a diagrammatic view of the diplexer section of the FIG. 1 apparatus.

The diplexer 54, shown in detail in FIG. 5, separates the transmitter heating frequency $\lambda T$ from the receiver center frequency $\lambda R$ which allows the use of the common coaxial cable connection 12 to the common antenna 16. Basically, the diplexer has two arms each of which contains a microwave filter. More particularly, the diplexer includes a low pass filter 72 at the output port of transmitter 52 which passes only the transmitter signal $\lambda T$ and a band pass filter 76 at the input port of the receiver 56 which passes the receiver signal $\lambda R$ but blocks the out-of-band transmitter signal $\lambda T$. To further isolate the two signals, filter 72 is positioned a quarter wavelength (at $\lambda R$) from the junction 74 of the diplexer. This creates a low-loss, well-matched stub at that frequency. Likewise, the length of the connection of filter 76 to junction 74 is a quarter wavelength (at $\lambda T$) so that the arm acts as a short circuit. Resultantly, the transmitter signal is not coupled to the receiver arm of the diplexer (and vice versa), thereby minimizing transmission losses.

As mentioned above, after catheter 10 is positioned in the patient's blood vessel V, the stand-off device 18 is opened to space antenna 16 from the vessel wall to avoid tissue damage due to radiation from the antenna. It is quite important, then, for the physician to know the condition of the stand-off device 18, i.e., whether it is open or closed. Accordingly, the present apparatus includes novel means for indicating to the physician the condition of the device 18.

As shown in FIG. 2, the microwave transmitter 52 incorporates two directional couplers 63a and 63b to sample both forward and reflected power. These sampled outputs are applied to two detectors 64a and 64b, respectively shown in FIG. 2 which provide video samples of the forward and reflected power. The detectors operate in their squarewave region which means that each detector output is proportional to the microwave power in watts. In the case of forward power, the detector 64a output is summed in a summing circuit 66a with the output from an adjustable DC offset source 68a, gained in an operational amplifier 72a and applied to a computational circuit 74 which is basically a one-quadrant divider with a fixed scale factor. For reflected power, the detector 64b output is summed at 66b with a DC offset voltage from adjustable source 68b, gained in an amplifier 72b and applied to circuit 74. The output of circuit 74 is given by $$V_0 = 2(P_{FWD})$$

where:

$V_0$ is the multiplier output in volts applied to the % reflected power meter, $P_{REFL}$ is the detected reflected power, and $P_{FWD}$ is the detected forward power.

The circuit 74 output, which is proportional to the power ratio, is applied to a power meter 76 which thereupon displays the % of forward power reflected, and is thus an indication of the reflection coefficient or load match to the transmitter 52. If desired, the function of circuit 72 could be incorporated into processor 58 and the meter 76 incorporated into display 62 to simplify the control and display unit 14.

The measurement of reflected power, i.e. the meter 76 reading, is used to determine the position of the stand-off device 18 (i.e., open or closed). More particularly, the antenna 16 will be well matched when device 18 is in the open position, allowing the high dielectric/high loss fluid (i.e., in this case, blood), to be closer to the antenna 16. In the closed position of device 18, the low dielectric/low loss plastic of device 18 will displace the blood producing an impedance mismatch and higher reflected power. The measured power difference shown by the power meter 56 provides a positive determination of, and indication to the physician of, the condition of the stand-off device, assuring that power will not be applied to antenna 16 if device 18 is closed and the catheter 10 is not spaced properly from the wall of blood vessel V.

One could also determine the condition of stand-off device by observing the amount of cord 22, e.g., number of beads 26, protruding from the end of fitting branch 15a in FIG. 1. Such an indicator is less desirable, however, because the cord could become separated from end segment 42b of sleeve 42 thereby invalidating the indication.

As noted previously, the present method and apparatus may be used to warm or heat tissue as well as blood. For example, it may be used in the treatment of benign prostatic hyperplasia (BPH); see above-mentioned application Ser. No. 09/476,201.

In this event, it may be desirable to use more than one frequency to sense temperature, for example, two different frequencies. This is because plural-frequency radiometric sensing can provide temperature information from different tissue depths. Since it is known that depth of penetration, or reciprocally depth of detection, of microwave energy increases with decreasing microwave frequency, to achieve a significant depth differential, it is desirable to have a wide separation between the different temperature sensing or radiometer frequencies. The frequencies chosen should represent a compromise between the desired tissue penetration depth, radiation intensity, emissivity and resolution. However, a separation of microwave frequencies that is too wide may preclude the use of a common antenna as described above due to the inability to optimize antenna element performance over an appreciable bandwidth.

With dual-frequency radiometric sensing, it is also desirable to separate the radiometer frequency from the transmitter frequency to allow simultaneous transmission and reception as described above. This would, however, reduce the separation between the two receiver or radiometer frequencies (unless the second radiometer operated at a frequency less than the transmitter. Therefore, for radiometric sensing using more than one frequency it is necessary to provide active diplexing or time sharing rather than simultaneous transmission and reception for one of the receiver frequencies. This second receiver or radiometric frequency may be the same as, or close to, the frequency of the transmitter, e.g. 915 MHz.

Figure 6:
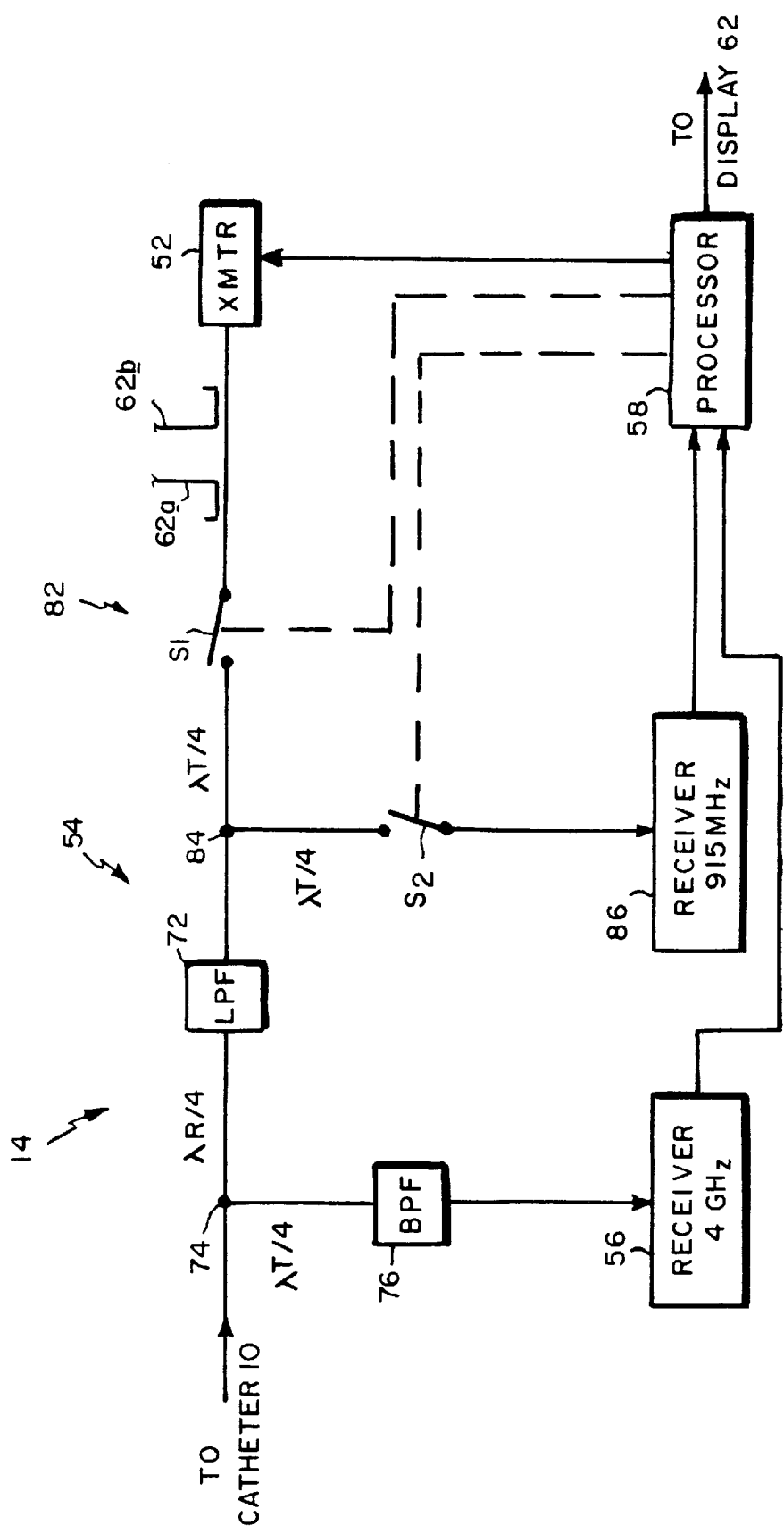
FIG. 6 is a diagrammatic view of a dual frequency microwave heating apparatus incorporating the invention.

FIG. 6 illustrates a circuit 14' similar to circuit 14 in FIG. 2 which is capable of heating tissue using microwaves having a first frequency and for measuring the actual tissue temperature at different depths by sensing emissions from the tissue at two different receiver or radiometer frequencies. The circuit elements in FIG. 6 that are in common with those in FIG. 2 carry the same identifying numerals.

As shown in FIG. 6, circuit 14', like circuit 14 in FIG. 2, includes a passive diplexer shown generally at 54 connected between catheter 10, transmitter 52 and receiver 56. Diplexer 54 may be the same as the one shown in FIG. 2. In this case, however, diplexer 54 is connected to transmitter 52 by way of an active diplexer shown generally at 82. Diplexer 82 comprises an SPST reflective switch $S_1$ connected between the transmitter and a junction 84 leading to the low pass filter 72 of diplexer 54. Diplexer 82 also includes a second SPST reflective switch $S_2$ connected between junction 84 and a second microwave receiver 86 which may be a radiometer operating at the frequency of transmitter 52, i.e. 915 MHz. Switches $S_1$ and $S_2$ may be solenoid switches controlled by processor 58.

The operation of the passive diplexer 54 is described above. The active diplexer 82 is basically a transmit/receive switch and is employed when the receiver frequency is at or near the transmitter frequency as is the case with the receiver 86 in circuit 14'.

When circuit 14' is operating in the transmit mode, switch $S_1$ is closed by processor 58 and switch $S_2$ is open thereby disconnecting the electrical path between junction 84 and receiver 86. Preferably, switch $S_2$ is positioned ¼ wavelength (at λT) from junction 84 of the diplexer to create a tuned ¼-wave stub at the junction. On the other hand, when circuit 14' is operating in the receive mode, switch $S_2$ is closed by the processor while switch $S_1$ is open, thus disconnecting the path from transmitter 52 while creating a tuned ¼-wave stub (at λT) at junction 84. Thus, the active diplexer 82 illustrated in FIG. 6 takes advantage of the ¼-wave spacing between the junction 84 and the switches. Since the transmitter and receiver 86 frequencies are the same, the ¼-wave lengths between the switches at junction 84 are identical.

The active diplexing or time sharing could also be accomplished by a single SPDT switch instead of a pair of SPST switches as shown. Such a switch would connect the filter 72 of the passive diplexer 54 alternatively to transmitter 52 or receiver 86. With such a modification, however, there would be no junction 84 and no tuned ¼-wave stubs to provide added frequency isolation as described above.

The FIG. 6 apparatus like the one depicted in FIG. 2 allows the use of a single or common antenna and catheter cable to both the transmitter and receivers. The diplexers and radiometers eliminate the need for thermocouples and wires thereby reducing catheter cost and improving catheter performance and safety. Moreover, the use of plural diplexers and receivers enables the apparatus to measure tissue temperature at different tissue depths so as to provide a maximum amount of information which is useful in some therapies, such as for the treatment of BPH.

It will thus be seen that the objects set forth above, among those made apparent from the preceding description, are efficiently attained. Also, certain changes may be made in carrying out the above method and in the construction set forth without departing from the scope of the invention. For example, in some applications, RF frequencies may be used for heating in which case the RF antenna should be matched at the radiometric frequency. Also, sleeve 42 comprising stand-off device 18 may be formed so that its ribs 42*a* are normally bowed outward as shown in FIGS. 3 and 4. So long as catheter 10 is in introducer 1 (FIG. 1), the stand-off device remains closed. However, when the stand-off device leaves the confines of the introducer, it automatically opens and when the catheter is retracted into the introducer, the device 18 is squeezed back to its closed position. Further, it is also possible for sleeve end segment 42*b* to be fixed and segment 42*a* movable. Therefore, it is intended that all matter contained in the above description or shown in the accompanying drawings shall be interpreted as illustrative and not in a limiting sense.

Having described the invention, what is claimed as new and secured by Letters Patent are:

What is claimed is:

1. Microwave heating apparatus for heating fluid or tissue, said apparatus comprising
    an elongated catheter for placement adjacent to high dielectric/high loss organic fluid or tissue in a patient, said catheter having a distal end and a proximal end and including an antenna adjacent to said distal end and a cable having one end connected to said antenna and a second end;
    a transmitter for producing a transmitter signal capable of heating said fluid or tissue;
    a first receiver for receiving a first signal having a first frequency indicative of thermal radiation from a first depth in said fluid or tissue and producing a first output signal in response thereto;
    a second receiver for receiving a second signal having a second frequency indicative of thermal radiation from a second depth in said fluid or tissue and producing a second output signal in response thereto;
    active and passive diplexers connected in series between said transmitter and the second end of said cable, said active diplexer including switch means operable between the transmitter, the passive diplexer and the second receiver;
    control means for controlling the switch means so that when the transmitter is transmitting, the transmitter signal is coupled to the passive diplexer but not to the second receiver and when the transmitter is not transmitting, any second signal from the passive diplexer is coupled to the second receiver but not to the transmitter, said passive diplexer coupling said transmitter signal received via the active diplexer only to said antenna, while coupling a first signal received from the antenna only to the first receiver so that the apparatus can heat said fluid or tissue and determine the actual temperature of the fluid or tissue at two different depths.

2. The apparatus defined in claim 1 wherein said first and second receivers comprise first and second radiometers.

3. The apparatus defined in claim 2 wherein said antenna is a monopole.

4. The apparatus defined in claim 1 wherein said transmitter signal has a lower frequency than said first signal.

5. The apparatus defined in claim 4 wherein the second signal has the same frequency as the transmitter signal.

6. The apparatus defined in claim 5 wherein the transmitter signal and the second signal have a frequency of about 915 MHz and the first signal has a frequency of about 4 GHz.

7. The apparatus defined in claim 1 wherein said passive diplexer comprises
    a first arm connected between the active diplexer and the cable second end and containing a low pass filter which passes only said transmitter signal, and
    a second arm connected between the first receiver and a junction between the low pass filter and the cable second end, said second arm containing a band pass filter which passes said first signal but blocks said transmitter signal.

8. The apparatus defined in claim 7 wherein the length of the connection between the low pass filter and the junction is ¼ wavelength at the frequency of the first signal and the length of the connection between the band pass filter and the junction is ¼ wavelength at the frequency of the transmitter signal.

9. The apparatus defined in claim 1 and further including a display responsive to said first and second output signals for producing indications of the actual temperatures of said fluid or tissue at said different depths.

10. The apparatus defined in claim 1 and further including control means responsive to at least one of said first and second output signals for controlling the transmitter to heat said tissue according to a selected temperature/time profile.

11. Microwave heating apparatus for heating fluid or tissue, said apparatus comprising an
    elongated catheter for placement adjacent to high/ dielectric high loss organic fluid or tissue in a patient, said catheter having a distal end and a proximal end and including an antenna adjacent to said distal end and a cable having one end connected to said antenna and a second end;
    a first receiver for receiving a first signal having a first frequency indicative of thermal radiation from a selected first depth in said fluid or tissue, and producing a first output signal in response thereto;
    a passive diplexer connected between the second end of said cable and said first receiver, said passive diplexer having an input terminal;
    a second receiver for receiving a second signal having a second frequency indicative of thermal radiation from a selected second depth in said fluid or tissue and producing a second output signal in response thereto;
    a transmitter for producing a transmitter signal at a frequency capable of heating said fluid or tissue;

an active diplexer including switch means for selectively connecting the input terminal of the passive diplexer alternatively to the transmitter or to the second receiver, and means for controlling the switch means so that when the transmitter is transmitting, the transmitter signal is coupled to the passive diplexer but not to the second receiver and when the transmitter is not transmitting, a second signal from the antenna is coupled to the second receiver but not to the transmitter, said passive diplexer coupling said transmitter signal from the transmitter only to said antenna while coupling a first signal from said antenna only to said first receiver so that the apparatus can simultaneously heat said fluid or tissue and determine the actual temperature of said fluid or tissue at said first and second depths.

12. The apparatus defined in claim 11 wherein said first and second receivers comprise first and second radiometers.

13. The apparatus defined in claim 11 wherein said active diplexer comprises
- a first SPST switch connected between the input of the active diplexer and the transmitter, and
- a second SPST switch connected between the input terminal of the passive diplexer and the second receiver, said switches being controlled by the controlling means.

14. The apparatus defined in claim 13 wherein the length of the connections between the input of the passive diplexer and each of said switches is ¼ wavelength at the frequency of the transmitter signal.

15. The apparatus defined in claim 11 wherein said active diplexer comprises an SPDT switch for connecting the input terminal of the passive diplexer alternatively to the transmitter or to the second receiver, said switch being controlling by the control means.

* * * * *